US006496733B2

(12) United States Patent
Zarinetchi et al.

(10) Patent No.: US 6,496,733 B2
(45) Date of Patent: Dec. 17, 2002

(54) TRANSCUTANEOUS ENERGY TRANSFER DEVICE WITH MAGNETIC FIELD PROTECTED COMPONENTS IN SECONDARY COIL

(75) Inventors: Farhad Zarinetchi, Chelmsford, MA (US); Robert M. Hart, Arlington, MA (US); Michael G. Verga, Newton, MA (US); Stephen J. Keville, Harvard, MA (US)

(73) Assignee: Abiomed, Inc., Danver, MA (US)

( * ) Notice: Subject to any disclaimer, the term of this patent is extended or adjusted under 35 U.S.C. 154(b) by 0 days.

(21) Appl. No.: 09/957,330

(22) Filed: Sep. 20, 2001

(65) Prior Publication Data

US 2002/0032472 A1 Mar. 14, 2002

Related U.S. Application Data

(60) Division of application No. 09/346,833, filed on Jul. 2, 1999, now Pat. No. 6,324,431, which is a continuation-in-part of application No. 09/110,607, filed on Jul. 6, 1998, now abandoned.

(51) Int. Cl.[7] ............................................... A61N 1/375
(52) U.S. Cl. ............................. 607/36; 607/61; 607/33
(58) Field of Search ........................... 607/1, 2, 36, 37, 607/34, 61

(56) References Cited

U.S. PATENT DOCUMENTS

| | | | |
|---|---|---|---|
| 3,195,540 A | 7/1965 | Waller | |
| 3,357,434 A | * 12/1967 | Abell | ........................... 607/61 |
| 3,824,129 A | 7/1974 | Fagan et al. | |
| 3,888,260 A | 6/1975 | Fischell | |
| 3,934,177 A | 1/1976 | Horbach | |

(List continued on next page.)

FOREIGN PATENT DOCUMENTS

| | | |
|---|---|---|
| DE | 2720011 | 11/1978 |
| EP | 0507360 | 7/1992 |
| JP | 7046164 | 2/1995 |
| WO | PCT/US99/15228 | 7/1999 |

OTHER PUBLICATIONS

Abe et al. "Development of Transcutaneous Energy Transmission System for Totally Implantable Artificial Heart" 1988.
Altieri et al. "Progress Towards a Totally Implantable Artificial Heart," *Cardiovascular Science & Technology: Basic & Applied, 1, Precised Proceedings* (1989–90).

(List continued on next page.)

*Primary Examiner*—George R. Evanisko
(74) *Attorney, Agent, or Firm*—Nutter, McClennen & Fish, LLP; Thomas Engellenner

(57) ABSTRACT

The invention provides a transcutaneous energy transfer device having an external primary coil and an implanted secondary coil inductively coupled to the primary coil, electronic components subcutaneously mounted within the secondary coil and a mechanism which reduces inductive heating of such components by the magnetic field of the secondary coil. For one embodiment of the invention, the mechanism for reducing inductive heating includes a cage formed of a high magnetic permeability material in which the electronic components are mounted, which cage guides the flux around the components to prevent heating thereof. For an alternative embodiment of the invention, a secondary coil has an outer winding and either a counter-wound inner winding or an inner winding in the magnetic field of the outer winding. For either arrangement of the inner coil, the inner coil generates a magnetic field substantially canceling the magnetic field of the outer coil in the area in which the electronic components are mounted.

19 Claims, 4 Drawing Sheets

U.S. PATENT DOCUMENTS

| | | | |
|---|---|---|---|
| 3,942,535 | A | 3/1976 | Schulman |
| 4,012,769 | A | 3/1977 | Edwards et al. |
| 4,041,955 | A | 8/1977 | Kelly et al. |
| 4,068,292 | A | 1/1978 | Berry et al. |
| 4,071,032 | A * | 1/1978 | Schulman ..................... 607/61 |
| 4,104,701 | A | 8/1978 | Baranowski |
| 4,186,749 | A | 2/1980 | Fryer |
| 4,441,498 | A | 4/1984 | Nordling |
| 4,517,585 | A | 5/1985 | Ridout et al. |
| 4,539,433 | A | 9/1985 | Ishino et al. |
| 4,586,508 | A | 5/1986 | Batina et al. |
| 4,665,896 | A | 5/1987 | LaForge et al. |
| 4,679,560 | A | 7/1987 | Galbraith |
| 4,741,339 | A | 5/1988 | Harrison et al. |
| 4,944,299 | A | 7/1990 | Sulvian |
| 5,000,178 | A | 3/1991 | Griffith |
| 5,214,392 | A | 5/1993 | Kobayashi et al. |
| 5,312,439 | A | 5/1994 | Loeb |
| 5,324,316 | A | 6/1994 | Schulman et al. |
| 5,358,514 | A | 10/1994 | Schulman et al. |
| 5,411,537 | A | 5/1995 | Munshi et al. |
| 5,527,348 | A | 6/1996 | Winkler et al. |
| 5,621,369 | A | 4/1997 | Gardner et al. |
| 5,951,459 | A | 9/1999 | Blackwell |
| 6,048,601 | A | 4/2000 | Yahagi et al. |
| 6,389,318 | B1 | 5/2002 | Zarinetchi et al. |

OTHER PUBLICATIONS

Bearnson et al. "Electronics Development for the Utah Electrohydraulic Total Artificial Heart," *Sixth Annual IEEE Symposium on Computer–Based Medical Systems,* 247–252 (1993).

Callewaert et al. "A Programmable Implantable Stimulator with Percutaneous Optical Control," *Ninth Annual Conference of the Engineering Medical and Biology Society IEEE,* 1370–1371 (1987).

Fraim et al. "Performance of a Tuned Ferrite Core Transcutaneous Transformer," *IEEE Transactions on Biomedical Engineering,* BME–18(5):352–59 (1971).

Galbraith et al. "A Wide–Band Efficient Inductive Transdermal Power and Data Link with Coupling Insensitive Gain," *IEEE Transactions on Biomedical Engineering,* BME 34(4):265–275 (1987).

Mitamura et al. "A Transcutaneous Optical Information Transmission System for Implantable Motor–Driven Artificial Hearts," *ASAIO Transactions,* 36(3):M278–280, (1990).

Mitamura et al. "Development of an Implantable Motor–Driven Assist Pump System," *IEEE Transactions and Biomedical Engineering,* 37(2):146–156 (1990).

Mitamura et al. "Development of Motor Driven Assist Pump Systems," *IEEE Ninth Conference of the Engineering and Medicine and Biology Society,* 184–185 (1987).

Mohammed et al. "A Miniature DC–DC Converter for Energy Producing Implantable Devices," *IEEE Ninth Annual Conference of the Engineering in Medicine and Biology Society,* 1147–1148, (1987).

Mohammed et al. "Design of Radio Frequency Powered Coils for Implantable Stimulators," *IEEE Ninth Annual Conference of the Engineering in Medicine and Biology Society,* 1378–1379 (1987).

Myers et al. "A Transcutaneous Power Transformer," *Transactions of the American Society for Artificial Internal Organs,* (1968).

Phillips "A High Capacity Transcutaneous Transmission System," *ASAIO Journal* 41;m259–m262 (1995).

Product Description from Raychem of HeatPath GTQ 1540.

Rintoul et al. "Continuous Development of the Cleveland Clinic–Nimbus Total Artificial Heart," *ASAIO Journal* 39:M168–171 (1993).

Sherman et al. "Transcutaneous Energy Transmission (TET) System for Energy Intensive Prosthetic Devices," *Progress in Artificial Organs* 1985:400–404.

Sutton "A Miniaturized Device for Electrical Energy Transmission Through Intact Skin–Concepts and Results of Initial Tests," *Third Annual Meeting of the International Society for Artificial Organs* 5 abstracts (Jul. 1981).

Weiss et al. "A Telemetry System for the Implanted Total Artificial Heart and Ventricular Assist Device," *IEEE Ninth Annual Conference of the Engineering in medicine and Biology Society* 186–187 (1987).

Weiss et al. "Permantent Circulatory Support Systems at the Pennsylvania State University," *IEEE Transaction on Biomedical Engineering* 37(2):138–145 (Feb. 1990).

Geselowitz et al. "The Effects of Metals on a Transcutaneous Energy Transmission System," *IEEE Transactions on Biomedical Engineering,* vol. 37, No. 2, Feb. 1990, pp. 928–934.

Miller et al. "Development of an Autotuned Transcutaneous Energy Transfer System," *ASAIO Journal,* Slide Forum—Prosthetics 5, 1993, pp. M706–M710.

Mitamura et al. "Development of Transcutaneous Energy Transmission System," *International Symposium on Artificial Heart and Assist Device,* $2^{nd:}$ 1987: Tokyo, Japan.

Mussivand et al. "Transcutaneous Energy Transfer System Performance Evaluation," *Artificial Organs,* vol. 17, No. 11, Blackwell Scientific Publications, Boston, May 1993, pp. 940–947.

Mussivand et al. "Remote Energy Transmission for Powering Artificial Hearts and Assist Devices," Cardiovascular Devices Div., Univ. of Ottawa Heart Institute, Ontario, pp. 344–347 (Publication Date Unknown).

Sherman et al., "Energy Transmission Across Intact Skin for Powering Artificial Internal Organs," *Trans. Am. Soc. Artificial Intern Organs,* vol. XXVII, 1981, pp. 137–141.

D.Del. Civil Action No. 98–41 (RRM) Daily transcript for Jan. 24, 2000.

D.Del. Civil Action No. 98–41 (RRM) Daily transcript for Jan. 26, 2000.

D.Del. Civil Action No. 98–41 (RRM) Daily transcript for Jan. 27, 2000.

D.Del. Civil Action No. 98–41 (RRM) Daily transcript for Jan. 28, 2000.

D.Del. Civil Action No. 98–41 (RRM) Daily transcript for Jan. 31, 2000.

D.Del. Civil Action No. 98–41 (RRM) Daily transcript for Feb. 1, 2000.

D.Del. Civil Action No. 98–41 (RRM) Daily transcript for Feb. 3, 2000.

D.Del. Civil Action No. 98–41 (RRM) Daily transcript for Feb. 4, 2000.

D.Del. Civil Action No. 98–41 (RRM) Deposition transcript of Robert T.V. Kung on Apr. 8, 1999.

D.Del. Civil Action No. 98–41 (RRM) Deposition transcript of Robert T.V. Kung on Apr. 9, 1999.

D.Del. Civil Action No. 98–41 (RRM) Deposition transcript of Farhad Zarinetchi on Apr. 7, 1999.

D.Del. Civil Action No. 98–41 (RRM) Deposition transcript of Farhad Zarinetchi on Aug. 25, 1999.

D.Del. Civil Action No. 98–41 (RRM) Deposition transcript of Burt Ochs on Apr. 28, 1999.

D.Del. Civil Action No. 98–41 (RRM) Deposition transcript of Robert T.V. Kung on Aug. 26, 1999.

D.Del. Civil Action No. 98–41 (RRM) Deposition transcript of Farhad Zarinetchi on Jan. 7, 2000.

D.Del. Civil Action No. 98–41 (RRM) Deposition transcript of Burt D. Ochs on Jan. 7, 20001.

D.Del. Civil Action No. 98–41 (RRM) Deposition transcript of Craig Sherman on Jan 7, 2000.

D.Del. Civil Action No. 98–41 (RRM) Deposition transcript of Mark N. Horenstein on Jan. 17, 2000.

* cited by examiner

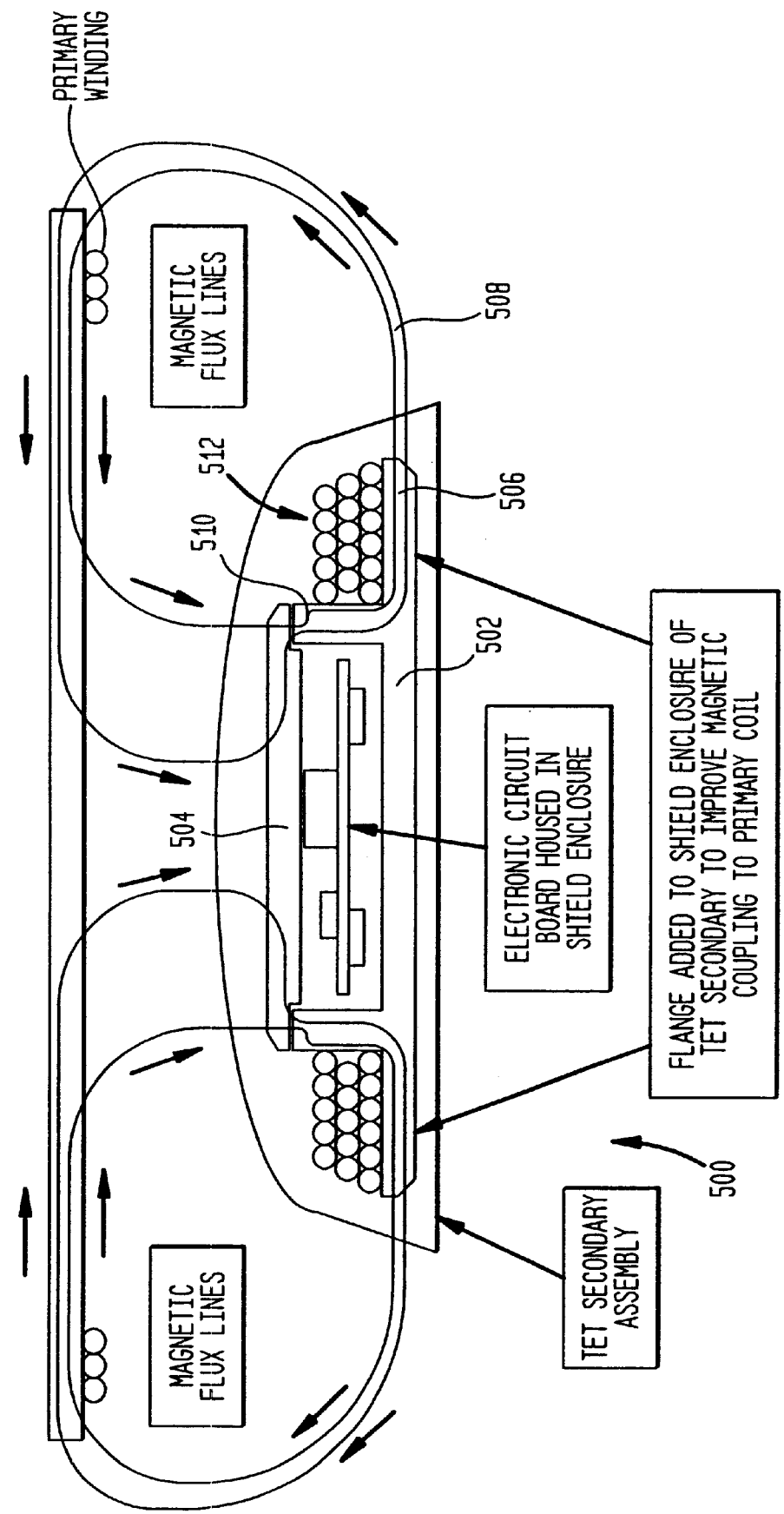

TRANSCUTANEOUS ENERGY TRANSFER DEVICE WITH MAGNETIC FIELD PROTECTED COMPONENTS IN SECONDARY COIL

RELATED APPLICATION

This application is a divisional application of U.S. patent application Ser. No. 09/346,833 filed Jul. 2, 1999 now U.S. Pat. No. 6,324,431 entitled "TRANSCUTANEOUS ENERGY TRANSFER DEVICE WITH MAGNETIC FIELD PROTECTED COMPONENTS IN SECONDARY COIL," and naming as inventors Fred Zarinetchi, Robert M. Hart and Steven J. Keville, which is a continuation-in-part of U.S. patent application Ser. No. 09/110,607 filed Jul. 6, 1998 entitled "TET WITH MAGNETIC FIELD PROTECTED COMPONENTS IN SECONDARY COIL," and naming as inventors Fred Zarinetchi and Robert M. Hart, now abandoned.

FIELD OF THE INVENTION

This invention relates to transcutaneous energy transfer (TET) devices and, more particularly, to such a device which includes a mechanism for protecting components mounted within a secondary coil from magnetic field induced heating.

BACKGROUND OF THE INVENTION

Many medical devices are now designed to be implantable including pacemakers, defibrillators, circulatory assist devices, cardiac replacement devices such as artificial hearts, cochlear implants, neuromuscular simulators, biosensors, and the like. Since almost all of the active devices (i.e., those that perform work) and many of the passive devices (i.e., those that do not perform work) require a source of power, inductively coupled transcutaneous energy transfer (TET) and information transmission systems for such devices are coming into increasing use. These systems consist of an external primary coil and an implanted secondary coil separated by an intervening layer of tissue.

One problem encountered in such TET systems is that the best place to locate control circuitry for converting, amplifying and otherwise processing the signal received at the secondary coil before sending the signal on to the utilization equipment is within the secondary coil itself. However, there is also a significant magnetic field in the secondary coil resulting from the current induced therein, which field can induce heating of the components, particularly metallic components. As a minimum, such heating can influence the performance of various components, and in particular interfere with the desired uniform power applied to the equipment. In a worst case, the heating can be severe enough to cause damage or destruction to the components which can only be repaired or replaced through an invasive surgical procedure. Such heating can also cause injury or discomfort to the patient in which the components have been implanted.

Heretofore, in order to avoid such heating, it has either been necessary to be sure that the signal induced in the secondary coil is not sufficient to generate a magnetic field which would cause potentially damaging heating of the components or to mount the components at a less convenient location. The former is undesirable because it is generally not possible to eliminate significant heating of the components while still operating the device at required energy levels, and the later solution is not desirable since the output signal from the secondary coil can reach 500 volts and above at an operating frequency that can be in excess of 100 kHz. It is preferable that such high voltage signal not pass extensively through the body and it is difficult to provide good hermetically sealed connectors for signals at these voltages. It is therefore preferable that an auxiliary signal processing module, which may reduce the voltage to a value in the approximately 20 volt range, be included as close to the secondary coil as possible, a position inside the secondary coil being ideal for this purpose.

A need therefore exists for an improved technique for use with TET devices so as to enable at least selected electronic components to be mounted within the secondary coil with minimal heating of such devices.

SUMMARY OF THE INVENTION

In accordance with the above, this invention provides a transcutaneous energy transfer device which includes an external primary coil to which energy to be transferred is applied, an implanted secondary coil inductively coupled to the primary coil, each of the coils generating a magnetic field, and electronic components subcutaneously mounted within the secondary coil, with a mechanism being provided which reduces inductive heating of such components by the magnetic field of the secondary coil. For one embodiment of the invention, the mechanism for reducing inductive heating includes a cage formed of a high magnetic permeability material in which the electronic components are mounted. The material of such cage is preferably a ferromagnetic material such as a ferrite and is preferably sufficiently thick so that magnetic field values in the material are well below saturation and so that significant heat dissipation in the material does not occur. The material of the cage should however be as thin as possible while satisfying the above criteria. The cage may be thicker in areas of the cage experiencing high flux density and thinner in other areas. The cage may also be formed of a layer of ferromagnetic material laminated with at least one layer of a low magnetic conductivity material to enhance flux guidance.

Alternatively, the mechanism may include winding the secondary coil with a first number $N_1$ of outer windings and a second number $N_2$ of counter-wound inner windings, $N_1$ being larger than $N_2$. $N_1$, $N_2$ and the diameters of both the outer and inner windings are selected such that the magnetic field caused by the coils in the region of the components is reduced sufficiently to prevent significant component heating. For a preferred embodiment, $N_1$, $N_2$, and the diameters of the windings are selected so that the magnetic fields caused by the windings substantially cancel in the region of the components. For an illustrative embodiment, $N_1$ is approximately 19, $N_2$ is approximately 7, and the diameter of the outer winding is approximately 2.5 inches, and the diameter of inner winding is approximately 1.5 inches. Alternatively, the inner windings may be in the magnetic field of the outer winding, but not electrically connected thereto.

In another aspect of the invention, a transcutaneous energy transfer device is disclosed. The TET includes an external primary coil; an implantable secondary coil coupled to the primary coil; a cage formed of a high magnetic permeability material located within the secondary coil to reduce inductive heating of electronic components mounted therein caused by a magnetic field of the primary and secondary coils, wherein the cage has walls of varying thickness such that a lowest total mass is achieved without exceeding the saturation density of the cage material. In one embodiment, the thickness of the cage walls is a minimum thickness that results in magnetic flux density through the cage walls is approximately equal to the saturation density.

In another aspect of the invention, another transcutaneous energy transfer device is disclosed. This TET includes an external primary coil; an implantable secondary coil coupled to the primary coil; and a cage formed of a high magnetic permeability material located within the secondary coil to reduce inductive heating of electronic components mounted therein caused by a magnetic field of the primary and secondary coils, wherein the cage has a geometry configured to maximize permeability in flux pathway between the primary and secondary coils. In one embodiment, the cage has flanges that extend the high permeability shield material within the flux pathway.

In another embodiment of this aspect of the invention, the cage includes a cylindrical base; a lid shaped in the form of a disk; and the flanges integral with the base. The flanges extend a high magnetic permeable region from base into the magnetic flux pathway. Preferably, the flange is in-line with a shortest flux pathway between the primary and secondary coils, such as extending from base immediately adjacent to the secondary coil to guide the magnetic flux lines back toward the primary coil.

In another aspect of the invention, a transcutaneous energy transfer device is disclosed. This TET includes an external primary coil; an implantable secondary coil coupled to the primary coil; and a cage formed of a high magnetic permeability material within the secondary coil to house electronic components. The cage includes a base; and a self-aligning lid.

In one embodiment of this aspect of the invention, the base is cylindrical and the lid is shaped in the form of a disk. In anther embodiment, the base includes vertical walls. The lid includes an annular recessed shelf circumferentially formed around a mating surface of the lid configured to receive the vertical wall of the base.

In a stiff further aspect of the invention, a transcutaneous energy transfer device is disclosed. The device includes an external primary coil; an implantable housing formed of a substantially low thermal conductivity medium; a secondary coil, mounted within the implantable housing, coupled to the primary coil; a cage formed of a high magnetic permeability material within the secondary coil to house electronic components; and a heat distribution layer thermally coupled to the cage and to an internal surface of the housing. The heat distribution layer may be comprised of multiple alternating layers of high and low heat conductivity materials.

In a further aspect of the invention, a transcutaneous energy transfer system is disclosed. The TET includes a primary coil and an implantable secondary coil having an outer first winding having a first number of turns and a first diameter and an inner second winding having a second number of turns and a second diameter. A method for determining the second number of turns, includes the steps of: a) winding the first winding with a predetermined number of turns; b) inserting a magnetic field monitoring device in a central region of the secondary coil; c) applying a dc current through the first winding while monitoring a magnetic field in the central region; d) winding the second winding in a direction a direction of the first winding using a wire extension from the first winding; e) monitoring, as the second winding is wound in the step d), a strength of a magnetic field in the central region; and f) stopping the winding of the second winding when the magnetic field strength reaches approximately zero.

Further features and advantages of the present invention as well as the structure and operation of various embodiments of the present invention are described in detail below with reference to the accompanying drawings. In the drawings, like reference numerals indicate like or functionally similar elements. Additionally, the left-most one or two digits of a reference numeral identifies the drawing in which the reference numeral first appears.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

FIG. 5 is a cross-sectional view of an alternative embodiment of a cage of the present invention having flanges or extensions extending therefrom.

DETAILED DESCRIPTION

Figure 1:
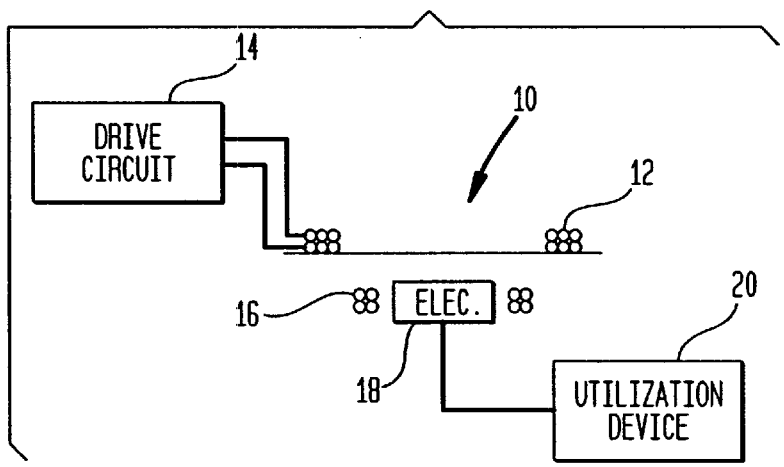
FIG. 1 is a schematic semi-block diagram of an exemplary TET system.

Referring to FIG. 1, an exemplary TET system 10 is shown which includes a primary coil 12 connected to receive an alternating drive signal from an appropriate drive circuit 14 and a transcutaneously mounted secondary coil 16 having signal processing electronics 18 mounted therein. The signal from electronics 18 is applied to operate a utilization device 20 which may for example be a blood pump, artificial heart, defibrillator, or other implanted device requiring power or other signals applied thereto. As illustrated in FIG. 4A, the magnetic field lines generated by the secondary coil 16 pass through the electronics 18 for the embodiment shown in FIG. 1, resulting in heating of the electronics and, in particular, metal portions thereof. This can cause undesired variations in the outputs from this device or, worst case, in component failure. In accordance with certain aspects of the present invention, FIGS. 2 and 3A–3C illustrate two techniques for reducing inductive heating of such electronic components 18 by the magnetic field generated by the primary and secondary coils.

Figure 2:
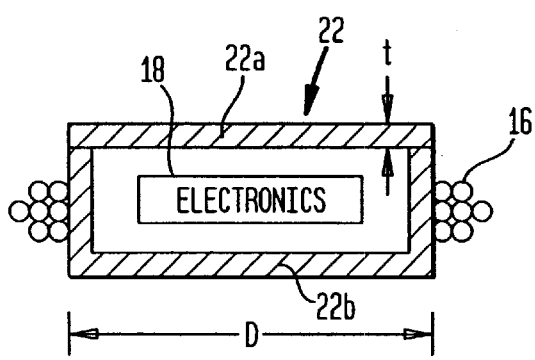
FIG. 2 is a cutaway sectional view of the secondary coil and electronics for a system of the type shown in FIG. 1 in accordance with a first embodiment of the invention.

Referring to FIG. 2, the electronics 18 are fully enclosed within a cage 22 formed of a high magnetic permeability material, the material for cage 22 preferably having a magnetic permeability in the range of approximately 2000–5000. Cage 22 is formed of a base 22A and a lid 22B which are fitted and held together in a manner known in the art which minimizes interruption of magnetic field lines passing through the cage. For a preferred embodiment, the material utilized for the cage is MnZn ferrite (Phillips 3F3), although other high magnetic permeability materials now or later developed may be used. The material is preferably one formulated for high frequency application with low power loss. Since it is desirable that cage 22 be as light (have minimal mass) as possible, the wall thickness (t) of the cage should be no thicker than is required to protect electronics 18 therein, preferably while minimizing heat loss. In particular, the thickness should be the minimum thickness for the material which provides magnetic field values in the material which are well below saturation, saturation preventing the flux from being guided effectively, and below the level that would lead to significant (for example, greater than 100 mw) heat dissipation in the material under operating conditions. Saturation in the cage is a function of magnetic field strength, while heat generation is a function of both magnetic field strength and frequency. For a ferrite cage material, the field strengths and frequencies at which these effects occur can be tabulated. With a give set of operating conditions, field strength or flux density increases with decreasing wall thickness. The magnetic field strength B may be determined by measurement at the top surface of the cage 22, and the total flux $\phi_t$ may be determined as the integral of B over the surface. This flux is guided through the side walls of the cage, density being highest in these side walls. The magnetic flux in the walls may then be calculated as the total flux divided by the cross sectional area of the wall:

$$B_{max} = \frac{\Phi_t}{(\pi D t)} \qquad \text{Eq. (1)}$$

A thickness t may be chosen so that $B_{max}$ is below the saturation level. In an alternative embodiment, the thickness t is also chosen so that the total heat dissipation at the operating frequency is less than 100 mw. In another embodiment, the thickness t is also chosen so that the total heat dissipation at the operating frequency is between 50 and 100 mw. In a still further embodiment, the thickness t is also chosen so that the total heat dissipation at the operating frequency is less than 150 mw. In a another embodiment, the thickness t is also chosen so that the total heat dissipation at the operating frequency is between 70–90 mw.

Figure 4A:
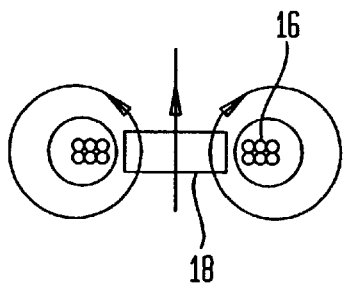
FIGS. 4A, 4B and 4C are side-sectional views of the secondary coil and electronics illustrating the magnetic field lines at the secondary for the embodiment shown in FIG. 1, FIG. 2, and FIGS. 3A–3C respectively.
Figure 4B:
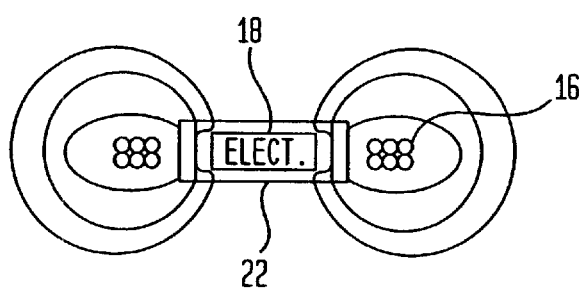

For an exemplary embodiment using the material previously indicated, wall thickness (t) is approximately 0.06 inches, and the diameter (D) of the cage for this embodiment is approximately 1.9 inches. However, these dimensions may vary significantly with application, for example the size of secondary coil 16, the electric energy applied thereto and the like. Further, the thickness of the cage need not necessarily be sufficient to divert all magnetic flux lines from the electronic 18 so long as it is effective to divert sufficient magnetic flux lines so as to prevent any significant heating of the electronic components. FIG. 4B illustrates the magnetic field for secondary coil 16 when a cage 22 of the type shown in FIG. 2 is employed. From FIG. 4B, it can be seen that the magnetic field is concentrated in the high permeability material of the cage so that the field at the electronic components 18 is reduced to nearly zero, with the magnetic field concentration being higher in the sidewalls of the cage than in the top and bottom walls. Thus, overall cage thickness and weight may in some instances be reduced by making the sidewalls thicker to accommodate the flux therein, with the top and bottom walls of the cage being thinner.

In one preferred embodiment, the optimal thickness of the cage wall has the lightest weight (lowest mass) without causing excessive heat dissipation. To have the lightest cage 22, the cage wall thickness is reduced, resulting in an increase in the magnetic flux density, B. To satisfy operation without excessive heat dissipation, B must be kept below the saturation density, $B_{max}$, for the selected cage material. Should $B_{max}$ be exceeded, the heat dissipation of the material increases dramatically. The combination of these two requirements, then, results in the, desired requirement that $B_0=B_{max}$, where $B_0$ is the flux density at the highest possible magnetic field strength for the device.

$B_0$ at any given point along the cage can be manipulated by varying the cage wall thickness. The design consideration is to reduce the cross sectional area of the cage so that $B_0$ is less than or equal $B_{max}$ along a substantial portion of the cage wall. An example of an algorithm for this process for a cylindrically symmetric cage includes first assuming a uniform thickness for the cage wall. Then, the total flux for highest power transfer within the cage walls, i.e. $\phi_0$ using the relationship $B_0=\phi_0/Lt$, where L is the perimeter of the cage 22 at the point of interest and t is the cage thickness wall. Given that L is determined by other design considerations, t can be adjusted so that $B_0=B_{max}$.

While for certain embodiments, the material of cage 22 is of a ferrite material, other high permeability materials might also be utilized such as, for example, laminated iron materials. For ease of fabrication, it may also be desirable to form the cage as three or more distinct segments, for example a top and bottom disk with a cylinder for the sidewalls, the disks and sidewalls being held together by a suitable epoxy, solder or other suitable means known in the art. This form of fabrication may be particularly desirable where the sidewalls are of a different thickness than the top and bottom walls. Preferably, the break in material continuity is minimized to avoid a significant reduction in the efficiency at which the magnetic field through the cage. Finally, forming the cage of alternate layers of ferrite material with high thermal and magnetic conductivity and epoxy or other similar material with low thermal and magnetic conductivity, results in a cage which is more anisotropic for magnetic flux flow, and thus provides potentially better flux guidance. In particular, such construction provides a lower reluctance path for the magnetic flux and magnetic fields through the ferrite layers then in a direction perpendicular thereto.

Figure 3A:
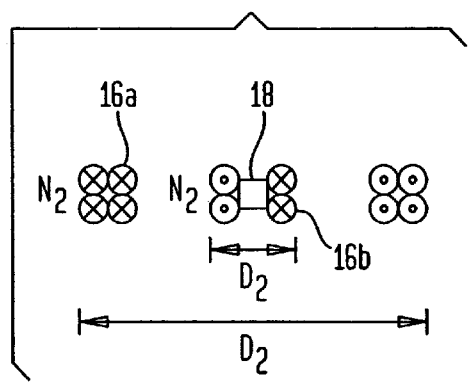
FIGS. 3A and 3B are a side-sectional view and a top plane view respectively of a secondary coil and electronics in accordance with a second embodiment of the invention.
Figure 3B:
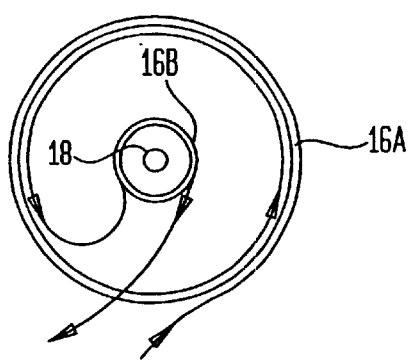

FIGS. 3A and 3B illustrate an alternative embodiment of the invention wherein reduced magnetic field at electronic components 18 is achieved by dividing the secondary coil into an outer coil 16A and an inner coil 16B which is counter-wound with the coil 16A so as to provide an opposing field. In this embodiment, the two sets of coils are connected so that the same current flows in each. The relative diameters of the two coils, $D_1$ and $D_2$ and the number of turns for the coils, $N_1$ and $N_2$, are adjusted so that their separate contributions to the total magnetic field at the location of components 18 significantly cancel each other. In achieving this objective, the field generated in the central region by a flat outer coil 16A is given,by:

$$B_2 = \frac{\mu N_1 i}{D_1} \qquad \text{Eq. (2)}$$

while the field generated by the inner coil 16B in the central region of the coil is given by:

$$B_2 = \frac{\mu N_2 i}{D_2} \qquad \text{Eq. (3)}$$

When the strengths of these two fields are selected to be equal, the ratio between the outer and inner windings becomes:

$$\frac{N_1}{N_2} = \frac{D_1}{D_2} \qquad \text{Eq. (4)}$$

Using these criteria with an illustrative embodiment where $D_1$=2.5 inches, $D_2$=1.5 inches and $N_1$=19, a value for $N_2$=11.4 would be obtained. However, for this implementation, because the inner coil was slightly elongated along the field direction, a preferred value for $N_2$ was found to be 7. Therefore, while the four values (the N and D values) can be calculated to achieve the desired magnetic field cancellation for a given application, it has been found to be easier and more accurate to select the parameters empirically, for example by selecting three of the parameters to achieve substantial field cancellation and then adjusting the fourth parameter until the field at the components 18 has been reduced so that there is no significant heating of the metal components thereof. Thus, assuming the other three values are given, an $N_2$ might be determined as follows:

1. Wind the outer coil with the predetermined number of turns (19 in the example given).
2. Insert a magnetic field monitoring device such as a gauss meter in the central region of the coil.
3. Apply a dc current through the outer coil and monitor the magnetic field in the central region.
4. Locate one of the ends of the outer coil and using the wire extension from this coil, start winding the inner coil in the opposite direction of the outer coil.
5. As the inner coil is wound, monitor the strength of the magnetic field in the central region. Stop winding the inner coil when this field reaches zero.

Other empirical procedures might similarly be used for determining the parameter values in order to achieve substantial field cancellation at the center of the coil.

Figure 4C:
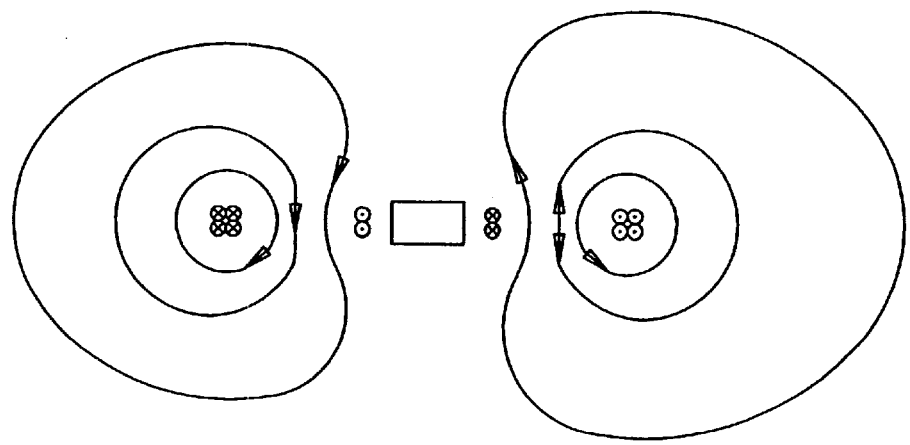

FIG. 4C illustrates a magnetic flux pattern which might be achieved with the winding pattern of FIGS. 3A–3B. From FIG. 4C, it can be seen that the magnetic field at components 18 can be reduced to substantially zero utilizing this technique. However, since this technique involves significant signal cancellation in the secondary coil, it results in a reduced energy transfer efficiency for the device. It may therefore not be suitable for use in applications where a high energy transfer efficiency is required.

Figure 3C:
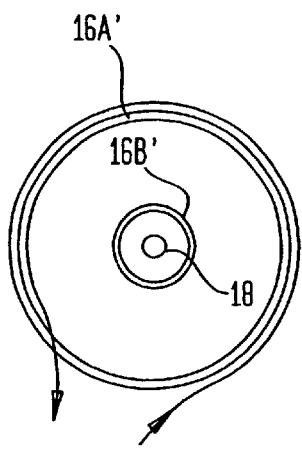
FIG. 3C is a top view for an alternative second embodiment.

FIG. 3C illustrates an alternative to the embodiment shown in FIG. 3B which to some extent reduces the loss of energy transfer efficiency resulting from the counter flowing current in coil 16B. For this embodiment, coil 16B' is a few turns of wire, for example one or two, having the diameter $D_2$ but not electrically connected to the windings 16A'. The magnetic flux resulting from current flow in windings 16A' induce a current in winding 16B' which in turn produce a magnetic field countering that generated by that winding 16A. By suitable selection of both the number and diameter of the windings 16A' and 16B', field cancellation such as that shown in FIG. 4C can be achieved.

In an alternative embodiment, the cage of the present invention is configured to increase the permeability in a flux pathway between the primary and secondary coils that is closest to the secondary coil. In one embodiment this is achieved by extending the high permeability shield material of cage 22 to a location within the flux pathway. This increases the total permeability of the flux pathway with a corresponding increase in coupling between the primary and secondary coils.

An exemplary implementation of this alternative embodiment of the cage is illustrated in FIG. 5. As shown therein, cage 500 includes a base 502 and a lid 504. In this illustrative embodiment, base 502 is cylindrical while lid 504 is shaped in the form of a disk. Base 502 includes and integral flange 506 that extends the cage material from base 502 into the magnetic flux pathway 508.

To increase the coupling between the primary and secondary coils, flange 506 is preferably in-line with the shortest flux pathway between the primary and secondary coils. In other words, flange 506 extends from base 502 immediately adjacent to secondary coil 512 to guide the magnetic flux lines back toward the primary coil. The extent to which the flange 506 extends away from base 502 is based on the mass and volume limitations of the device. However, flange 506 preferably does not have a thickness less than that which would cause saturation of the magnetic material, particularly at highest primary field strengths.

It should be understood that flange 506 may be the same or different high permeability material as base 502. In devices wherein flange 506 and cage 22 are of the same material, flange 506 and base 502 are preferably formed as a unitary device. However, in alternative embodiments, flange 506 may be attached to base 502 using well-known techniques.

Figure 6:
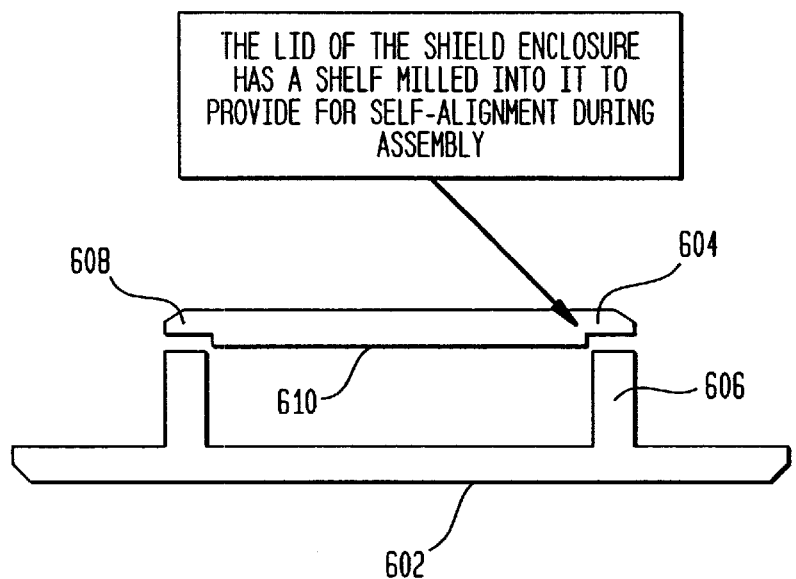
FIG. 6 is a simplified cross-sectional view of a cage in accordance with one embodiment of the present invention.

FIG. 6 is a simplified cross-sectional view of an alternative embodiment of a cage 600. Cage 600 includes a base 602 and an self-aligning or interlocking lid 604. In this illustrative embodiment, base 602 is cylindrical while lid 604 is shaped in the form of a disk. Base 602 includes vertical walls 606 onto which lid 604 is attached, typically by bonding.

Lid 604 includes an annular recessed shelf 608 circumferentially formed around mating surface 610 of lid 604. Shelf 608 is configured to receive vertical wall 606 of base 602 thereby preventing relative motion of lid 604 and base 602 during assembly. It should be understood that other features may be used to align and/or secure lid 604 with base 602, such as by threading, etc. Alternatively, mating surface 610 of lid 604 may have a track or groove configured to accept base vertical wall 606. It should also be noted that annual recessed shelf 608 may be configured as a square or any other shape to accept base 602.

Figure 7:
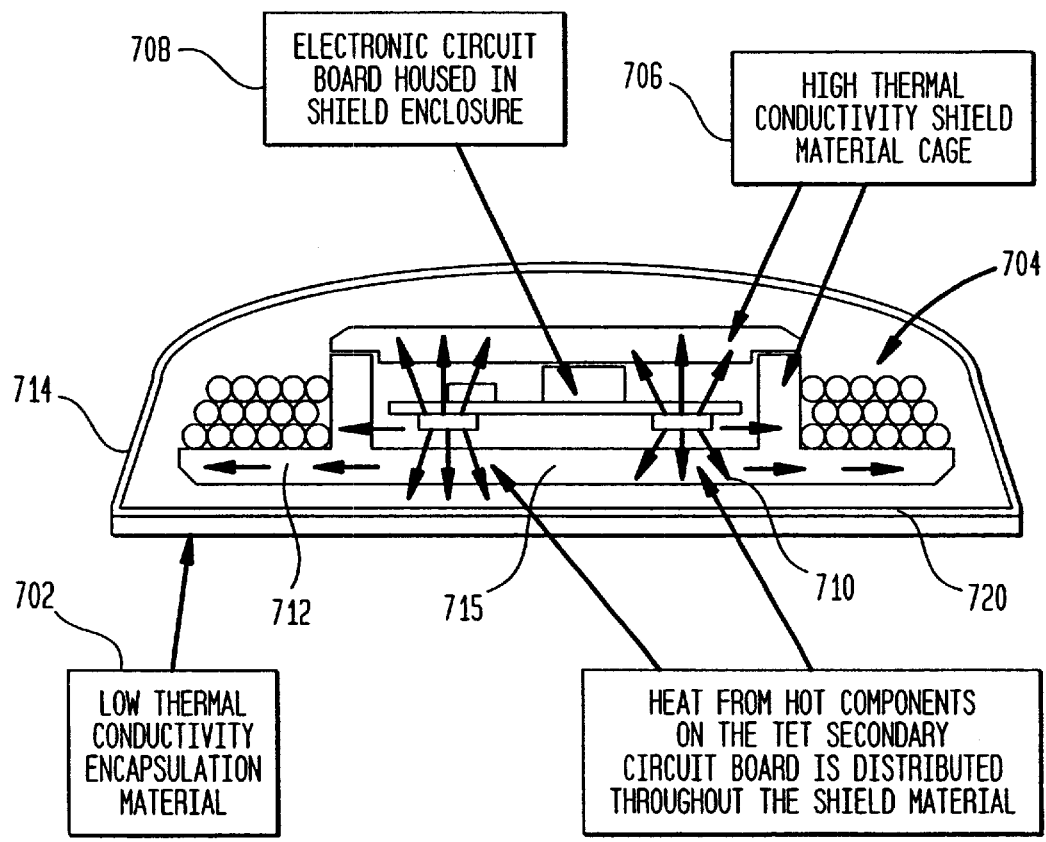
FIG. 7 is a cross-sectional view of an implantable device housing a secondary coil in accordance with an alternative embodiment of the present invention.

FIG. 7 is a cross-sectional view of an implantable device 702 housing a secondary coil 704. Cage 706 is positioned within secondary coil 704, as described above. Cage 706 serves to house electronic components 708 that generate heat, illustrated by arrows 710. In accordance with this embodiment of the present invention, heat in implanted device 702 is distributed to avoid localized high temperature regions as well as tissue necrosis.

Housing 702 is constructed of a relatively low thermal conductivity medium such as potting epoxy. Cage 706 preferably includes flange 712 similar to the flange described above with reference to FIG. 6. In accordance with this embodiment of the present invention, a heat distribution layer 714 is thermally coupled to cage 706 and housing 702. Heat generated by electronics 708 is transferred via conduction to cage 706. To facilitate the transfer of such heat into distribution layer 714 good thermal contact is maintained between distribution layer 714 and cage 706 using a thermally conductive medium. In addition, the largest contact area between distribution layer 714 and cage 706 suitable for the implemented design is implemented. For example, in the embodiment illustrated in FIG. 7, flange 712 provides base 715 with the greatest area over surface 720 as compared to other surfaces of cage 706. Accordingly, distribution layer 714 is thermally coupled to cage 706 at surface 720. Similarly, distribution layer 714 is preferably thermally coupled to a substantial area of housing 702. This provides for the substantially uniform distribution of heat along housing 702. In the embodiment illustrated in FIG. 7, distribution layer 714 is thermally coupled to the entire housing 702 other than the portion of housing 702 adjacent bottom surface 720 of cage 706.

In one embodiment, distribution layer 714 has a high thermal conductivity and a low magnetic permeability and low electrical conductivity. For example, in one preferred embodiment, distribution layer 714 is formed from alumina powder suspended in an epoxy medium. The thickness of the distribution layer 714 is preferably in the range of 2–10 mm, although other thicknesses and materials may be used for a given application. In an alternative embodiment, distribution layer 714 is comprised of multiple alternating layers of high and low heat conductivity materials.

While specific embodiments have been disclosed above for reducing the magnetic field at the center of a TET device secondary coil so as to permit device electronics to be mounted in the coil without excessive heating, it is to be understood that other techniques for achieving this objective and/or other variations on the embodiments disclosed are within the contemplation of the invention. Thus, while the invention has been particularly shown and described above with reference to preferred embodiments, the foregoing and other changes in form and detail may be made therein by one skilled in the art while still remaining within the spirit and scope of the invention which is to be defined only by the following claims.

Further information is described in currently pending U.S. patent application Ser. No. 09/110,607 filed Jul. 6, 1998 entitled "TET WITH MAGNETIC FIELD PROTECTED COMPONENTS IN SECONDARY COIL," and naming as inventors Fred Zarinetchi and Robert M. Hart, now currently pending, incorporated herein by reference in its entirety.

What is claimed is:

1. A transcutaneous energy transfer device comprising:
   an external primary coil adapted to receive an alternating drive signal for generating a magnetic field;
   an implantable secondary coil having mounted therein electronic components electrically coupled to the secondary coil, the secondary coil for inducing a current when the secondary coil is inductively coupled to the primary coil, the induced current in the secondary coil generating a magnetic field, the magnetic field of the primary and secondary coils including a magnetic flux pathway between the primary and secondary coils; and
   a cage mounted within the secondary coil and formed of a magnetically permeable material enclosing the electronic components to reduce inductive heating of the electronic components caused by the magnetic field of the primary and secondary coils;
   wherein the cage includes a base having at least one flange integral with the base and extending the magnetically permeable material from the base into the flux pathway.

2. The transcutaneous energy transfer device of claim 1, wherein the cage has a geometry configured to maximize permeability in the magnetic flux pathway between the primary and secondary coils.

3. The transcutaneous energy transfer device of claim 1, wherein the cage further comprises a lid configured to be received by the base to enclose the electronic components therein.

4. The transcutaneous energy transfer device of claim 3, wherein a flange is integrally provided on each of two opposed ends of the base.

5. The transcutaneous energy transfer device of claim 3, wherein the flange extends from the base immediately adjacent to the secondary coil to guide one or more lines of magnetic flux back toward the primary coil.

6. The transcutaneous energy transfer device of claim 3, wherein the lid is a self-aligning lid adapted to mate with a first end of the base.

7. The transcutaneous energy transfer device of claim 3, wherein the base includes vertical walls and wherein the lid includes an annular recessed shelf circumferentially formed around a mating surface of the lid configured to receive the vertical walls of the base.

8. The transcutaneous energy transfer device of claim 1, wherein the flange is in-line with a shortest flux pathway between the primary and secondary coils.

9. The transcutaneous energy transfer device of claim 1, further comprising a heat distribution layer thermally coupled to the cage and to the electronic components.

10. The transcutaneous energy transfer device of claim 9, further comprising a housing enclosing the secondary coil, cage and electronic components, the heat distribution layer being thermally coupled to the electronic components by a thermal contact with the housing.

11. The transcutaneous energy transfer device of claim 9, wherein the heat distribution layer is comprised of multiple alternating layers of high and low heat conductivity materials.

12. The transcutaneous energy transfer device of claim 9, wherein the heat distribution layer is thermally coupled to the flange.

13. The transcutaneous energy transfer device of claim 1, wherein the magnetically permeable material has high magnetic permeability in the range of approximately 2000–5000.

14. The transcutaneous energy transfer device of claim 1, wherein the magnetically permeable material is a ferrite.

15. The transcutaneous energy transfer device of claim 1, wherein the magnetically permeable material is laminated iron.

16. The transcutaneous energy transfer device of claim 1, wherein the cage includes a plurality of cage walls and the thickness of the cage walls is such that total heat dissipation is less than 150 mw at an operating frequency of approximately 100 kHz or more.

17. The transcutaneous energy transfer device of claim 16, wherein the thickness of the cage walls is such that total heat dissipation is less than 100 mw at an operating frequency of approximately 100 kHz or more.

18. The transcutaneous energy transfer device of claim 16, wherein the thickness of the cage walls is such that total heat dissipation is between 50 to 100 mw at an operating frequency of approximately 100 kHz or more.

19. The transcutaneous energy transfer device of claim 16, wherein the thickness of the cage walls is such that total heat dissipation is between about 70 to 90 mw at an operating frequency of approximately 100 kHz or more.

* * * * *

UNITED STATES PATENT AND TRADEMARK OFFICE
CERTIFICATE OF CORRECTION

PATENT NO.      : 6,496,733 B2
DATED           : December 17, 2002
INVENTOR(S)     : F. Zarinetchi et al.

It is certified that error appears in the above-identified patent and that said Letters Patent is hereby corrected as shown below:

<u>Title page,</u>
Item [56], U.S. PATENT DOCUMENTS, "4,944,299", "Sulvian" should be
-- Silvian --;

<u>Column 1,</u>
Line 49, "As a minimum" should be -- At a minimum --;

<u>Column 3,</u>
Line 36, "In a stiff further" should be -- In a still further --;
Line 59, "in a direction a direction of" should be -- in a direction of --;

<u>Column 4,</u>
Line 26, "the secondary for" should be -- the secondary coil for --;

<u>Column 5,</u>
Line 16, "With a give set" should be -- With a given set --;

<u>Column 6,</u>
Line 33, "magnetic field through" should be -- magnetic field is conducted through --;
Line 57, (Eq. 2), "B2" should be -- B1 --;

<u>Column 8,</u>
Line 5, "includes and integral" should be -- includes an integral --;
Line 28, "and an self-aligning" should be -- and a self-aligning --.

Signed and Sealed this

Nineteenth Day of August, 2003

JAMES E. ROGAN
*Director of the United States Patent and Trademark Office*